United States Patent [19]

Jaeger

[11] 4,133,210

[45] Jan. 9, 1979

[54] SAMPLING APPARATUS

[76] Inventor: Ben E. Jaeger, Rte. 2, Box 49, Plano, Ill. 60545

[21] Appl. No.: 880,698

[22] Filed: Feb. 23, 1978

[51] Int. Cl.² .............................................. G01N 1/10
[52] U.S. Cl. .................................................. 73/424
[58] Field of Search .............................. 73/424, 421 R

[56] References Cited

U.S. PATENT DOCUMENTS

| | | | |
|---|---|---|---|
| 2,654,249 | 10/1953 | Visman | 73/424 |
| 3,280,635 | 10/1966 | Cochet | 73/424 |
| 3,545,280 | 12/1970 | Gosney | 73/424 |

*Primary Examiner*—S. Clement Swisher
*Attorney, Agent, or Firm*—Gary, Juettner & Pyle

[57] ABSTRACT

A sampler for obtaining small samples of material from a flow of bulk material as it is transported past a sampling station, is characterized by a sample collecting scoop which is rotated in an arcuate path through the material about an axis inclined at an angle with respect to the major plane of the material. The scoop moves through the material generally in the direction of material flow and at a speed slightly greater than that of the flow, and by virtue of its inclined axis of rotation has components of motion therein both vertically and transversely of the material. In consequence, even if the material is segregated the sample obtained by the scoop is a true representation of the material. After leaving the material, the scoop is then rotated to a sample collection point above and transversely to the side of the material, whereat the sample is deposited in a container. A number of such samples obtained from different parts of the material flow may be combined to build a representative composite sample, which is then analyzed to determine the overall composition of the bulk of material.

16 Claims, 5 Drawing Figures

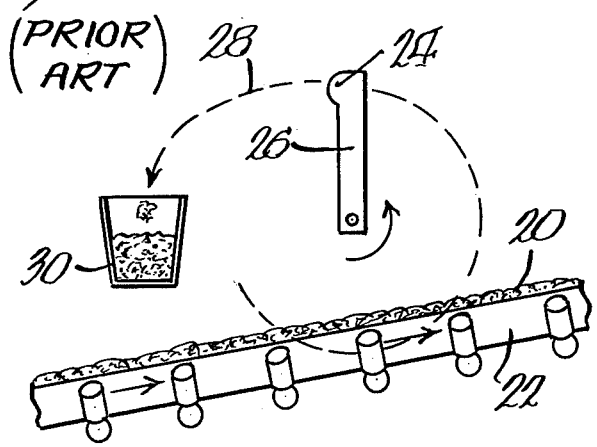
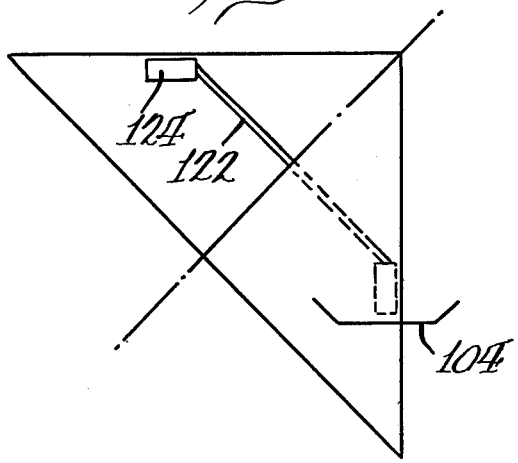
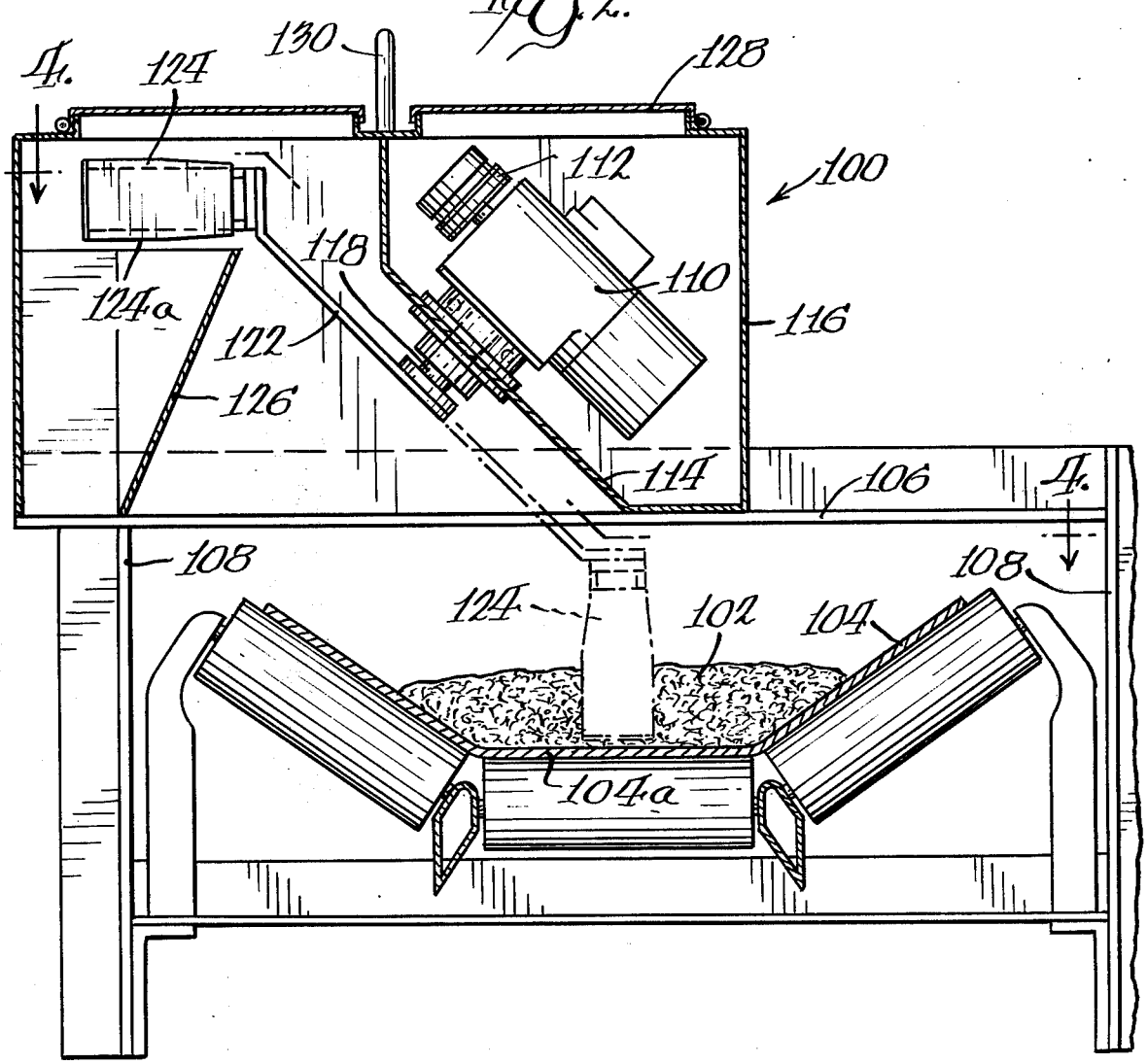

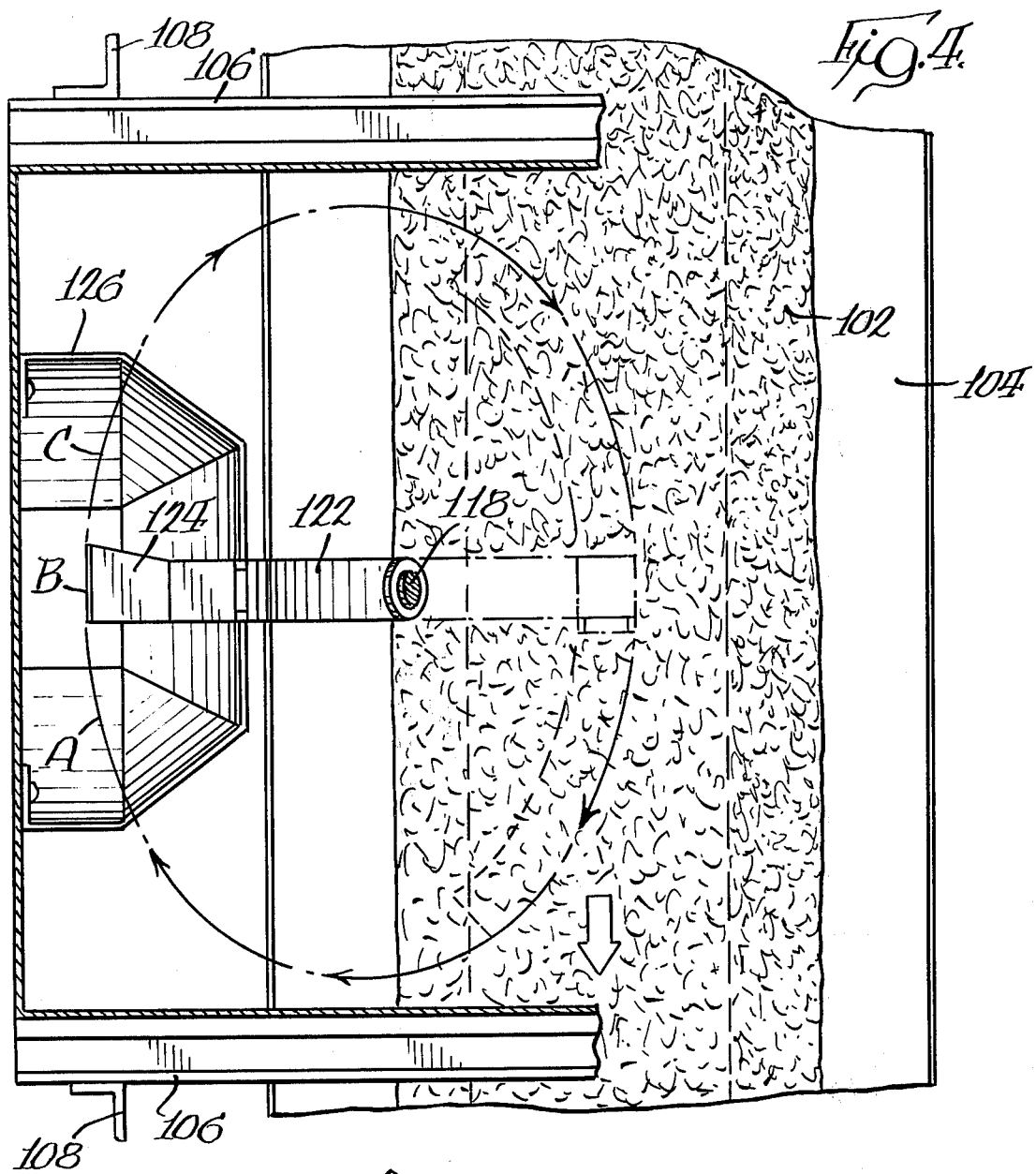
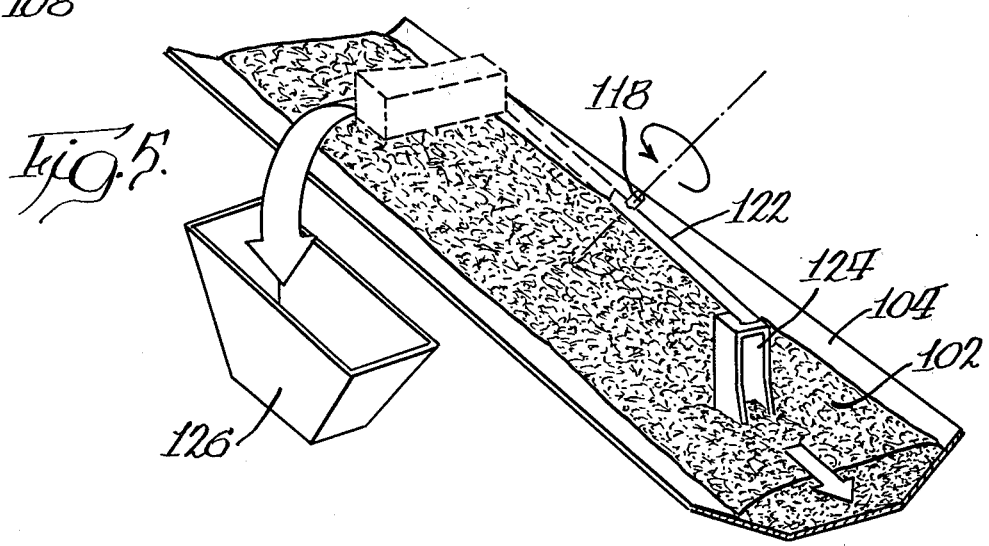

SAMPLING APPARATUS

BACKGROUND OF THE INVENTION

The present invention relates to an apparatus for obtaining a small quantity of material which is representative of the average of some large amount of the material, and in particular to an apparatus for cyclically obtaining and collecting small samples of heterogeneous granular material from a bulk of such material as it is transported past a sampling station.

In the manufacture or mining of heterogeneous granular materials, such as cement clinker, crushed ore, coal, phosphate rock and the like, which are composed of small lumps or particles differing in diameter and composition, the materials are often transported from one point to another by, for example, a belt-type conveyor. To determine the properties of these materials, it is common practice to take small samples therefrom and to analyze the samples.

Sampling may consist of periodically taking portions from a stream of material as it is transported past a sampling station. A number of samples obtained from different parts of the flow of bulk material are then combined to build a composite sample which is representative of the average of the total material flow. The contents of the composite sample are thoroughly mixed and perhaps crushed, whereafter a sample is taken therefrom of a size customary for analyzing.

The different sizes of granules of the heterogeneous bulk material to be sampled tend to segreate when the material is transported on a conveyor. On account of this segregation, some samplers have been designed to cut samples periodically from a stream of material discharging from an end of the conveyor by intermittent transverse movements across the stream. The length of these cuts depends upon the width of the stream of material, and therefore the size of every sample will be comparatively large if the stream is wide, as is usually the case with products transported in bulk. The composite sample will thus be undesirably large, and the greater accuracy which might be expected to result from a large total sample is not in fact attained due to the need to subsequently split the large sample to obtain a small sample suitable for analysis.

Another sampling technique is disclosed in U.S. Pat. No. 2,654,249. In the apparatus therein disclosed, a sample collecting tube is rotated through material on a conveyor in a direction against the movement of the material and about an axis extending across the material parallel to the major plane thereof and transversely of the direction of material flow. Because of the particular orientation of the axis of rotation, the tube moves through the material in a plane perpendicular to the major plane of the material and extending along its direction of movement, with the result that there is no component of movement of the tube transversely of the material, whereby samples of transversely segregated portions of the material are not obtained. In addition, because the tube moves against the direction of material movement, there is disruption of the material and scattering of the same off of the conveyor. After collecting the sample, the tube is rotated to an upper portion to cause the sample to fall through the tube for collection.

In another type of apparatus a scoop on an end of an arm is rotated through material on a conveyor and about an axis extending across the material parallel to the major plane thereof and transversely of its direction of movement. In this case, however, the scoop is moved through the material along its direction of flow, whereby disruption and scattering of the material is minimized. After collecting a sample, the scoop is then rotated to a position above the conveyor whereat movement thereof is abruptly stopped. This causes the sample of material to move out of the scoop, as a result of inertia, for collection in a suitable container positioned in its fall line.

The container, of course, must be positioned out of the plane of rotation of the scoop in order to avoid interference with either. The speed of the scoop approximately equals the speed of the material on the conveyor, and for conveyor speeds in excess of about 300 feet per minute such an arrangement is satisfactory since the inertia of the material is then sufficient to carry the material beyond the plane of rotation of the scoop and into the container. For conveyor speeds of less than 300 feet per minute, however, the inertia of the material is usually insufficient to carry it out of the plane of rotation of the scoop, with the result that at least some of the material falls back onto the conveyor.

In order to collect samples from slow moving conveyors, in a sampler somewhat similar to that just above described the arm supporting the scoop has a passage through which the material may travel for collection without being thrown out of the scoop. This technique is satisfactory for conveyor speeds of 200 feet per minute or less, since inertia does not then tend to move the material out of the scoop when the scoop is stopped. With conveyor speeds in excess of 200 feet per minute, however, at least some of the material is thrown out of the scoop as the same is stopped, whereby a portion if not all of the sample is lost. Consequently, neither type of apparatus is suitable for use with all conveyor speeds which might reasonably be encountered, and neither is entirely satisfactory where the speed is in the range of 200 to 300 feet per minute. In addition, since the scoop in each apparatus moves in a plane perpendicular to the major plane of the material and along the direction of movement thereof, there is no transverse movement of the scoop through the material and transversely segregated portions of the material are not sampled.

OBJECTS OF THE INVENTION

An object of the present invention is to provide an improved sampling apparatus for extracting discrete samples of a heterogeneous material, from a moving stream of a body of material, which accurately represent the composition of the body of material.

Another object of the invention is to provide such a sampling apparatus in which a scoop for obtaining a sample of the material is moved through the stream of material vertically, transversely and longitudinally thereof.

A further object of the invention is to provide such a sampling apparatus in which the scoop is rotated through the stream of material about an axis inclined with respect to the major plane of the material.

Yet another object of the invention is to provide such a sampling apparatus in which the plane of movement of the scoop lies along the surface of an inclined cone.

A still further object of the invention is to provide such a sampling apparatus in which the scoop is moved through the stream of material generally in the direction of flow thereof and at a speed slightly in excess of that of the flow in order to minimize disruption and scattering of the material.

SUMMARY OF THE INVENTION

In accordance with the present invention, a sampling apparatus for obtaining a multiplicity of small samples from a moving stream of materials comprises a sample collecting scoop and means for cyclically rotating the scoop through the stream of materials in an arcuate path which moves the scoop through the materials in directions longitudinally, transversely and vertically thereof.

Preferably, the apparatus is for cyclically obtaining a small sample of material from a moving body of material transported therepast, the body of material having a major plane extending along its direction of movement and transversely thereof. Rotating the scoop through the body comprises rotating the scoop about an axis that is inclined to the major plane, in order to move the scoop through the material in directions vertically of the material and parallel to and transversely of the direction of movement of the material to obtain a small sample of material from various positions therein. The axis is perpendicular to the direction of movement of the material, and the movement of the scoop parallel to the direction of movement of the material is in the same direction as the movement of the material and at a speed greater than the speed of the material. Rotation of the scoop is accomplished with a drive means having a rotatable output shaft extending along the axis and an arm secured at one of its ends to the shaft and extending perpendicularly therefrom, and the scoop is mounted to an opposite end of the arm. The drive means and the arm are above the body of material and rotate the scoop through substantially 360° with each cycle of operation of the sampler. The axis is inclined at an angle of substantially 45° with respect to the major plane, and the scoop has a long dimension and is mounted on the arm with its long dimension at an angle of substantially 45° to the arm, so that when the scoop is in its lowermost position the long dimension extends generally vertically of, and when the scoop is in its uppermost position the long dimension extends generally parallel to, the major plane.

A container for receiving each sample is positioned with an opening thereto above and transversely to the side of the body of material, and the drive means moves the scoop to above the opening, after moving the scoop through the body of material, for discharge of the sample in the scoop through the opening. In accordance with one embodiment of the invention, to discharge the sample from the scoop the drive means operates to rapidly stop movement of the scoop at a point above the opening to cause the sample to leave the scoop by its own inertia and to pass through the opening for collection in the container. In another embodiment of the invention, the drive means rotates the scoop to a point above the container opening whereat the scoop is tipped down, and then stops movement of the scoop to pour the sample therefrom and into the opening. In both embodiments, by virtue of the unique orientation of the axis of rotation of the scoop with respect to the major plane of the body of material, and of the scoop with respect to the arm, the drive means rotates the scoop through a path defining an inclined frusto-conical surface.

The foregoing and other objects, advantages and features of the invention will become apparent upon a consideration of the following detailed description, when taken in conjunction with the accompanying drawings.

BRIEF DESCRIPTION OF THE DRAWINGS

FIG. 1 is a highly schematic side elevation view of a conventional sampling apparatus for obtaining samples of material from a stream of material transported therepast;

FIG. 2 is a side elevation view, partly in cross section, of a sampling apparatus embodying the teachings of the present invention, illustrating the axial orientation of the apparatus with respect to a stream of material transported therepast;

FIG. 3 is a graphic illustration of the surface defined by a sampling scoop of the apparatus as it is rotated into and out of the stream of material;

FIG. 4 is a plan view taken substantially along the lines 4—4 of FIG. 2, and shows the movement of the sampling scoop with respect to the stream of material and between the stream and a sample collecting container, and FIG. 5 is a fragmentary perspective view illustrating the sampling scoop in its positions for obtaining a sample of material from the stream of material and for dumping the sample into the container, the remainder of the apparatus being omitted for the purpose of clarity.

DETAILED DESCRIPTION

In order to better appreciate the advantages and features of the present invention, reference is first made to FIG. 1 in which is shown in highly schematic form a sampling apparatus representative of those disclosed by the prior art. The apparatus is for taking discrete samples of material from a moving stream of material 20 transported therepast on a conveyor 22, and includes a scoop 24 on an arm 26 which is periodically rotated to move the scoop through the stream. The arm rotates about an axis that is parallel to the major plane of the material and transverse to the direction of movement thereof, the major plane being considered as extending laterally of the stream of material and along its direction of flow, whereby the scoop is rotated through a plane extending perpendicular to the major plane of the material and along the direction of movement thereof. The direction and speed of rotation of the arm are adjusted so that the scoop moves through the material in its direction of flow at a speed slightly in excess of its flow rate.

Often the material to be sampled is comprised of heterogeneous granular materials, such as crushed ore, coal, phosphate rock and other like materials. The different sizes of granules of the material tend to segregate when the material is transported on a conveyor, with discrete segregated portions of the material occurring both from top to bottom and from side to side in the stream. Consequently, to obtain a sample which accurately represents the average composition of the body of material, the scoop ideally should move through the stream both from top to bottom and from side to side. Unfortunately, because of the particular orientation of the axis of rotation of the scoop with respect to the stream of material, only the vertically segregated portions of the material are sampled, not those transversely segregated. Accordingly, the sample of material collected by the scoop is not truely representative in composition of the average composition of the body of material.

During sampling, the arm 26 is rotated at a constant speed about its axis. With this arrangement, one technique for collecting the samples in the scoop contemplates rapidly stopping rotation of the arm when the scoop is in an elevated position. This causes the sample of material, as a result of its inertia, to move out of the scoop and along a path indicated at 28 to a container 30 for collection. When a sufficient number of samples have been collected, the composite sample is thoroughly mixed for analyzing. To the extent that the individual samples represent true cross sections of the material on the belt, the composite sample is representative of the average of the body of material.

Note that the container must be positioned out of the plane of rotation of the scoop to avoid interference with either when the scoop is rotated. Since the scoop moves at substantially the same speed as the conveyor, for speeds in excess of about 300 feet per minute the inertia of the sample is sufficient to carry it out of the plane of rotation and to the container. For slower conveyor speeds, however, the inertia of the sample is insufficient to carry the entire sample to the container, and at least a portion of the sample falls back onto the conveyor.

To obtain samples from slowly moving conveyors, apparatus has been provided in which the material in the scoop is collected by gravity through a passage in the arm. In this case, upon the scoop being stopped in an elevated position, the material moves downward through the passage in the arm to a container at an end of the arm toward its axis. This arrangement is suitable for obtaining samples of material from conveyors moving at speeds less than about 200 feet per minute, since at those speeds the inertia of the sample is insufficient to cause it to move from the scoop when the scoop is stopped, whereby the entire sample flows through the passage.

For conveyor speeds between about 200 to 300 feet per minute, however, neither of such prior art samplers satisfactorily transfers material from the scoop to a collecting container, since at those speeds the scoop is not moving fast enough to enable the entire sample to be tossed into a container, but is nevertheless moving sufficiently fast to cause some of the material to be tossed out of the scoop.

To overcome the aforementioned disadvantages of prior art samplers, the invention provides a sampling apparatus in which a scoop for obtaining samples from a stream of material transported past a sampling station is moved longitudinally through the stream in the same direction as the flow thereof and at a speed slightly in excess of the flow rate, and in directions both vertically and transversely of the material. When used to obtain samples of heterogeneous granular materials, this movement of the scoop along three axes enables the scoop to obtain samples of the various segregated portions of the material, whereby each individual sample is a true representation of the average of the material then moving past the sampling station.

Such composite movement of the scoop through the stream of material is obtained by rotating the scoop about an axis that is inclined with respect to the major plane of the stream or body of material, preferably at an angle of about 45°, and perpendicular to the direction of movement. Rotating the scoop about an inclined axis also provides the advantage that after a sample of material is collected in the scoop, further rotation of the scoop moves the same above and transversely to the side of the stream, whereat a container may be positioned for receiving the sample. Consequently, in the sample discharge position of the scoop the container is always beneath the scoop, so that the material may either be tossed or dumped into the container without loss of any of the sample.

More particularly, and with reference to FIG. 2, there is indicated generally at 100 a material sampling apparatus embodying the teachings of the present invention. The apparatus is adapted to cyclically or periodically extract a discrete sample of material from a stream of material 102 being transported past a sampling station on a conveyor 104, the stream having a direction of movement out of the drawing for the orientation of the apparatus shown. The apparatus is supported generally above the stream on a pair of beams 106 extended between legs 108 connected with opposite sides of the conveyor frame, and includes a gear reducer 110 having a pulley 112 on an input shaft thereof connected through a belt with a pulley on an output shaft of a motor (not shown). The gear reducer is mounted on a support plate 114 within a housing 116, and has an output shaft 118 extending at an angle inclined with respect to the major plane of the stream of material, which may be considered as extending transversely and longitudinally of the stream parallel to a lower planar surface 104a of the conveyor. Particular advantages have been obtained when the output shaft 118 lies in a plane that is perpendicular to the major plane of the stream of material and extends transversely thereacross, with the shaft being inclined at an angle of about 45° with respect to the major plane of the material, as will be described.

With reference also to FIGS. 4 and 5, the sample collecting portion of the apparatus comprises an arm 122 having a scoop 124 at one end thereof. An opposite end of the arm is attached to the output shaft 118 and extends perpendicularly therefrom, and the scoop may comprise an elongated rectangular box-like housing having an open forward end for receiving samples of material. The scoop is secured to the one end of the arm with its long axis at an angle of about 45° with respect to the arm, whereby the scoop extends generally vertically when rotated to its lowermost position and generally horizontally when rotated to its uppermost position.

A sample collecting container 126 is mounted on a side wall of the housing 116, and has an open upper end extending beneath the scoop 124 when the scoop is rotated to an elevated position. The opening is relatively elongate in the direction of movement of the scoop thereacross, and by virtue of the inclined axis of rotation of the scoop and its mounting on the arm at an angle, the scoop is free to travel over and around the container without interference to either. The container, scoop, arm, gear reducer and motor are all contained within the housing 116 for safety, and a cover 128, which may be raised by means of a handle 130, normally closes the housing to prevent any possibility of injury to attending personnel, yet may be lifted to expose the interior of the housing for servicing. To this end, interlocks (not shown) advantageously may be provided to disable the apparatus whenever the cover is removed from the housing, and for further safety the container may be provided with a chute extending to exterior of the housing for removal of the samples without the need to enter into the housing.

In the use of the apparatus to obtain discrete samples of the material 102, the scoop 124, which normally is maintained in an upper position, is rotated 360° through the stream of material to collect the sample and then back to its upper position for depositing the sample in the container. In the case where heterogeneous materials are to be sampled, the different sizes of granules of the material tend to segregate and be variously positioned both vertically and transversely of the stream of material. Consequently, to obtain a sample that truely represents the average of the material, the scoop ideally should obtain the sample from various vertical and transverse locations in the material.

It may now be appreciated that the mounting of the scoop in accordance with the teachings of the invention enables the scoop to obtain a sample that truly represents the average of the material. In particular, the motor and gear reducer rotate the scoop through the stream of material generally in the direction of flow thereof and at a speed slightly in excess of the flow rate of the stream, whereby the scoop has a component of movement longitudinally of the stream of material. From FIG. 3 it is seen that the rotating scoop defines an inclined frusto-conical surface, and in conjunction with FIGS. 4 and 5 it may be understood that this provides a vertical component of movement of the scoop into and out of the stream of material as well as a lateral component of movement transversely of the stream. In consequence, upon each cycle of operation of the sampler apparatus the scoop is moved through the stream of material longitudinally, vertically and transversely thereof to obtain a sample from the various segregated portions of material.

The motor is of a type which may rapidly be braked to stop rotation of the scoop. Thus, where the flow rate of the material is in excess of about 300 feet per minute, the speed of the scoop is sufficient to cause the entire sample of material, upon rapid braking of the motor, to move from the scoop as a result of inertia. Accordingly, with such conveyor speeds the sample may be ejected from the scoop by rapidly stopping the scoop as it begins to pass over the upper end of the container 126, as for example at point A in FIG. 4, whereupon the sample will fall into the container. At this point, a lower side wall 124a of the scoop is inclined upwardly, but the inertia of the sample is nevertheless sufficient to carry the sample from the scoop.

For flow rates of the material stream less than about 300 feet per minute, the speed of the scoop may not be sufficient to cause the sample to be moved therefrom by inertia. Consequently, for slower conveyor speeds the motor is braked to stop movement of the scoop at a point further over the opening to the container, as for example at point B whereat the wall 124a of the scoop is generally horizontal, or even at the point C whereat the wall is inclined downwardly to enable the sample to fall or be poured out of the scoop. Accordingly, irrespective of the speed at which the stream of material is being transported, the position at which the scoop is stopped above the container may be adjusted to ensure complete ejection of the sample from the scoop and collection of the sample in the container.

The invention thus accommodates both inertia ejection and pouring of a sample from the scoop with a single apparatus. To this end, it is to be noted that whenever the scoop is in an upper sample discharge position, the container for collecting the sample is always directly beneath the scoop. This ensures that the entire sample is always removed from the scoop and collected, without any loss of the sample outside of the container as often occurs with conventional sampling apparatus.

In view of the composite movement of the scoop longitudinally, vertically and transversely of the stream of material during its movement therethrough, the apparatus is particularly adapted to sample heterogeneous granular materials, since upon each sampling cycle the scoop will be moved through the various segregated portions of the material and the sample will be a true representation of the average of the larger body of material. The apparatus may readily be adapted for automatic control, whereby sampling cycles are initiated at predetermined intervals, for example from twice per minute to once every thirty minutes. After a number of such samples have been obtained from different parts of the material and combined to form a gross sample, the contents of the gross sample may be thoroughly mixed and analyzed to provide an accurate and true representation of the average composition of the larger amount of material. In addition, the movement of the scoop through the material from side to side may readily be selected so that the scoop either passes through the longitudinal center of the material or remains to one side thereof, in accordance with whichever movement provides a more representative sample of the material.

While embodiments of the invention have been described in detail, various modifications and other embodiments thereof may be devised by one skilled in the art without departing from the spirit and scope of the invention, as defined by the appended claims.

What is claimed is:

1. A sampling apparatus for obtaining a multiplicity of small samples from a moving stream of materials, comprising a sample collecting scoop, and means for cyclically rotating said scoop through said stream of materials in an arcuate path which moves said scoop through said materials in directions transversely and vertically thereof and longitudinally at a speed differing from that of the material.

2. A sampling apparatus for obtaining a multiplicity of small samples from a moving stream of materials, comprising a sample collecting scoop, and means for cyclically rotating said scoop through said stream of materials in an arcuate path which moves said scoop through said materials in directions longitudinally, transversely and vertically thereof, said means for rotating comprising means for rotating said sample collecting scoop about an axis which is inclined to the major plane of said materials, said major plane extending longitudinally and transversely of said stream of materials.

3. A sampling apparatus as set forth in claim 2, said axis of rotation being perpendicular to the direction of movement of said stream of materials.

4. A sampling apparatus for obtaining a multiplicity of small samples from a moving stream of materials, comprising a sample collecting scoop, and means for cyclically rotating said scoop through said stream of materials in an arcuate path which moves said scoop through said materials in directions longitudinally, transversely and vertically thereof, said sample collecting scoop being moved longitudinally through said stream of materials along the direction of movement of said stream of materials and at a speed slightly greater than the speed of said materials, said scoop having an opening facing its direction of movement.

5. A sampling apparatus as set forth in claim 2, said sample collecting scoop normally being positioned above said stream of materials, said rotating means rotating said scoop through substantially 360° with each cycle of operation for obtaining a sample, and including means for receiving each sample from said scoop.

6. A sampling apparatus as set forth in claim 2, said axis of rotation being inclined at substantially 45° to the major plane of said stream of materials, and including an arm for mounting said sample collecting scoop for rotation about said axis, said arm extending perpendicularly from said axis and said scoop being elongate and being connected at a longitudinal end thereof with said arm at an angle of substantially 45° so that said scoop extends generally vertically when in its lowermost position and generally horizontally when in its uppermost position, said rotating means rotating said scoop through 360° with each cycle of operation of said sampler and the path of said scoop defining an inclined frusto-conical surface.

7. A sampling apparatus for cyclically obtaining a small sample of material from a moving body of material transported therepast, said body of material having a major plane extending along its direction of movement and transversely thereof, comprising a sample collecting scoop, and means for rotating said scoop through said body of material about an axis inclined to said major plane to move said scoop through said material in directions vertically of said material and parallel to and transversely of the direction of movement thereof to obtain a small sample of material therefrom.

8. A sampling apparatus as set forth in claim 7, said axis being perpendicular to the direction of movement of said body of material.

9. A sampling apparatus as set forth in claim 7, said movement of said scoop parallel to the direction of movement of said body of material being in the same direction as the movement of said material and at a speed greater than the speed of said material.

10. A sampling apparatus as set forth in claim 7, said means for rotating comprising drive means having a rotatable output shaft extending along said axis and an arm secured at one of its ends to said shaft and extending perpendicularly therefrom for rotation therewith, said scoop being mounted to an opposite end of said arm for rotation by said drive means.

11. A sampling apparatus as set forth in claim 10, said drive means and arm being above said body of material and said drive means rotating said arm through substantially 360° with each cycle of operation of said sampler to obtain said sample, and including means positioned above and transversely to the side of said body of material for receiving said sample from said scoop.

12. A sampling apparatus as set forth in claim 10, said axis being perpendicular to the direction of movement of said body of material and at an angle of substantially 45° with respect to said major plane, said scoop rotating through said material generally along the direction of movement thereof and at a speed slightly faster than the speed of said material, said scoop having a long dimension and being mounted on said arm with said long dimension at an angle of substantially 45° to said arm so that when said scoop is in its lowermost position said long dimension extends generally vertically, and when said scoop is in its uppermost position said long dimension extends generally horizontally, of said major plane.

13. A sampling apparatus as set forth in claim 10, including a container for receiving each said sample, said container having an opening positioned above and transversely to the side of said body of material, said drive means moving said scoop to above said opening after moving said scoop through said body of material for discharge of the sample through said opening.

14. A sampling apparatus as set forth in claim 13, said drive means rotating said scoop through said body of material to obtain a sample thereof and then to a point above said container opening, said drive means operating to rapidly stop movement of said scoop at said point to cause said sample to leave said scoop by its own inertia and to pass through said opening for collection in said container.

15. A sampling apparatus as set forth in claim 13, said drive means rotating said scoop through said body of material to obtain a sample thereof and then to a point above said container opening whereat said scoop is tipped down, said drive means then operating to stop movement of said scoop to pour said sample therefrom and into said opening for collection in said container.

16. A sampling apparatus as set forth in claim 13, said drive means rotating said scoop through a path defining an inclined frusto-conical surface.

* * * * *